United States Patent [19]

Collipp

[11] 4,148,906
[45] Apr. 10, 1979

[54] GROWTH HORMONE INHIBITORS

[75] Inventor: Platon J. Collipp, 299 Vanderbilt Pkway., Dix Hills, N.Y. 11746

[73] Assignee: Platon J. Collipp, Dix Hills, N.Y.

[21] Appl. No.: 895,731

[22] Filed: Apr. 13, 1978

Related U.S. Application Data

[63] Continuation-in-part of Ser. No. 865,905, Dec. 30, 1977, abandoned.

[51] Int. Cl.$^2$ .................. A61Y 31/415; A61Y 31/505
[52] U.S. Cl. ................................ 424/273 R; 424/251
[58] Field of Search ............................... 424/273, 251

[56] References Cited

PUBLICATIONS

Chem. Abst. 82-132779, (1975).
Chem. Abst. 76–Chem. Substance Inc. E–O under 3H–Imidazo [2,1a] isoindol 5–ol (1972).

*Primary Examiner*—Stanley J. Friedman
*Attorney, Agent, or Firm*—Gerald D. Sharkin; Robert S. Honor

[57] ABSTRACT

Certain known imidazo[2,1-a]isoindoles and imidazo [2,1-a]isoquinolines, e.g., 5-(p-chlorophenyl)-5-hydroxy-2,3-dihydro-5H-imidazo[2,1-a]isoindole (mazindol), have been found to be useful as growth hormone inhibitors in mammals.

6 Claims, No Drawings

GROWTH HORMONE INHIBITORS

This application is a continuation-in-part of application Ser. No. 865,905, filed Dec. 30, 1977, now abandoned.

This invention relates to the use of known substituted imidazo[2,1-a]isoindoles and imidazo[2,1-a]isoquinolines in inhibiting the growth hormone activity in mammals.

The active compound with which this invention is concerned may be represented by the following structural formula

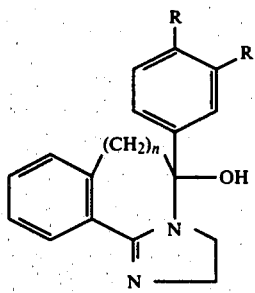

where
n represents 0 or 1,
each R, independently, represents hydrogen or halo of atomic weight about 19 to 36, or a pharmaceutically acceptable acid addition salt thereof.

As will be appreciated by persons skilled in this art, the acid addition salt forms of certain of the compounds (I) may actually involve a tautomeric or modified form of the above structure in salt form, but in order to simplify this description, and although both forms are intended to be included, reference will only be made in the specification and claims to the compounds (I) and salts thereof.

The compounds of formula (I) are known and may be prepared according to methods disclosed in various patents and publications in the United States and foreign countries, e.g., The Journal of Organic Chemistry, 33, No. 7, July 1968, pp. 2874–2877. As indicated above, the present invention contemplates only the novel use of such compounds particularly as agents useful in inhibiting growth hormone activity in mammals. The use of the imidazo[2,1-a]isoindoles is a preferred aspect of this invention, and the preferred compound for this use is 5-(p-chlorophenyl)-5-hydroxy-2,3-dihydro-5H-imidazo[2,1-a]isoindole (mazindol).

The compounds of formula (I) are useful in regulating growth hormone in mammals as indicated by daily administration of 2 milligrams of mazindol, the preferred compound of formula (I), to a group of 17 children between 5 and 15 years of age for one year. The height of the patients was measured for one year post-treatment and for the year during which mazindol was administered. The growth of the patients in the year during mazindol administration averaged 0.6 inches whereas the average growth for the year post-treatment was 1.5 inches. Moreover, assays of growth hormone in the two patients so assayed showed significant reduction of growth hormone in the blood serum after mazindol administration.

The compounds (I) with which this invention is concerned, by inhibiting growth hormone activity, may accordingly be utilized in the treatment of conditions such as acromegaly, retinal angiopathy, or microangropathy, or the compounds may be used to help regulate the growth rate of mammals, such as humans and especially human females of adolescent age.

As will be appreciated by one skilled in the art in view of the above, compounds (I) may also be utilized in conjunction with other chemical agents known to have an effect on regulating growth hormone activity. Accordingly, compounds (I) may be used with compounds such as somatostatin or chemical and biological analogs thereof so as either to avoid or lessen an undesirable side effect of just one of the drugs used along or to improve the effect otherwise available from just the single drug.

For use as growth hormone inhibitors, compounds (I) may be administered, preferably orally or parenterally, as such or admixed with conventional pharmaceutical carriers. They may be administered orally in such forms as tablets, dispersible powders, granules, or capsules, or as oral liquids, e.g., oral liquid suspensions, syrups, and elixirs, parenterally as solutions, suspensions, dispersions, emulsions, and the like, e.g., a sterile injectable aqueous suspension, and as suppositories, etc. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g., starch and aliginic acid, binding agents, e.g., starch, gelatin and acacia, and lubricating agents, e.g., magnesium stearate, stearic acid and talc. The tablets may be uncoated or coated by known techniques or be otherwise prepared so as to dely disintegration and absorption in the gastrointestinal tract and thereby provide a sustained action over a longer period. Similarly, suspensions syrups and elixirs may contain the active ingredient in admixture with any of the conventional excipients utilized for the preparation of such compositions, e.g., suspending agents (methyl-cellulose, tragacanth and sodium alginate), wetting agents (lecithin, polyoxyethylene stearate and polyoxyethylene sorbitan mono-oleate) and preservatives (ethyl--hydroxyl-benzoate). Capsules may contain the active ingredient alone or admixed with an inert solid diluent, e.g., calcium carbonate, calcium phosphate and kaolin. The injectable compositions are formulated as known in the art and may contain appropriate dispersing or wetting agents and suspending agents identical or similar to those mentioned above. These pharmaceutical preparations may contain up to about 90% of the active ingredient in combination with the carrier or adjuvant.

Furthermore, the compounds of formula (I) may be similarly administered in the form of their corresponding non-toxic pharmaceutically acceptable acid addition salts. Such salts possess the same order of activity as the respective free base, are readily prepared by reacting the base with an appropriate acid and accordingly are included within the scope of the invention. Representative of such salts are the mineral acid salts, such as the hydrochloride, hydrobromide, sulfate, phosphate and the like and the organic acid salts, such as the succinate, maleate, fumarate, acetate, p-toluenesulfonate, and the like.

The dosage of active ingredient employed for inhibiting growth hormone may vary depending on the particular compound (I) employed and the severity of the condition being treated.

However, in general, satisfactory results are obtained when the active compound is administered preferably orally, at a daily dosage of from about 0.01 milligram to about 50 milligrams per kilogram of animal body weight, preferably given in divided doses two to four times a day, or in sustained release form. For most large mammals, the total daily dosage is from about 0.5 to 5 milligrams. Dosage forms suitable for internal use comprise from about 0.125 to about 2.5 milligrams of the active compound (I) in intimate admixture with a solid or liquid pharmaceutically acceptable carrier of diluent.

The preferred pharmaceutical compositions from the standpoint of preparation and ease of administration are tablets or capsules containing about 0.5 to 3 milligrams of active ingredient.

EXAMPLES 1 and 2

Tablets and Capsules Suitable for Oral Administration.

Tablets and capsules containing the ingredients indicated below may be prepared by conventional techniques and are useful in inhibiting growth hormone activity at a dose of one tablet of capsule two to four times a day.

| INGREDIENT | WEIGHT (mg.) | |
|---|---|---|
| | Tablet | Capsule |
| mazindol | 1 | 1 |
| tragacanth | 10 | — |
| lactose | 246.5 | 298 |
| corn starch | 25 | — |
| talcum | 15 | — |
| magnesium stearate | 2.5 | — |

The compounds 5-(3,4-dichlorophenyl)-5-hydroxy-2,3-dihydro-5H-imidazo[2,1-a]isoindole, 5-(3-fluorophenyl)-5-hydroxy-2,3-dihydro-5H-imidazo[2,1-a]isoindole, 5-(p-fluorophenyl)-5-hydroxy-2,3,5,6-tetrahydroimidazo[2,1-a]isoquinoline, or 5-hydroxy-5-phenyl-2,3-dihydro-5H-imidazo[2,1-a]isoindole may be used in place of mazindol for these formulations of Examples 1 and 2.

What is claimed is:

1. A method for inhibiting growth hormone activity in a mammal which comprises administering to a mammal in need of said treatment an effective amount of a compound of the formula

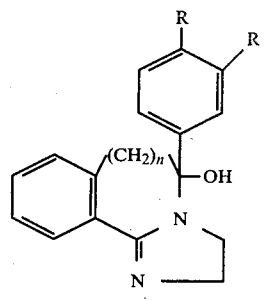

wherein
n is 0 or 1,
each R, independently, represents hydrogen or halo of atomic weight about 19–36, or a pharmaceutically acceptable acid addition salt thereof.

2. A method according to claim 1 in which the compound is 5-(p-chlorophenyl)-5-hydroxy-2,3-dihydro-5H-imidazo[2,1-a]isoindole.

3. A method according to claim 1 wherein the compound is administered to a mammal in need of said treatment at a daily dose of from about 0.5 milligrams to about 5 milligrams.

4. A method according to claim 1 wherein the compound is administered to a mammal in need of said treatment in a unit dosage form comprising said compound to the extent of from about 0.125 milligrams to about 2.5 milligrams per unit dosage.

5. A method for inhibiting the growth of a mammal which comprises administering to a mammal in need of said treatment an effective amount of a compound of the formula

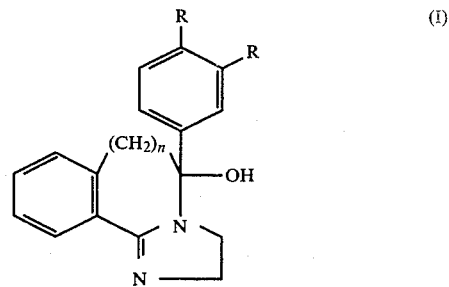

where
n represents 0 or 1,
each R, independently, represents hydrogen or halo of atomic weight about 19 to 36, or a pharmaceutically acceptable acid addition salt thereof.

6. A method according to claim 5 in which the compound is 5-(chlorophenyl)-5-hydroxy-2,3-dihydro-5H-imidazo[2,1-a]isoindole.

* * * * *

UNITED STATES PATENT AND TRADEMARK OFFICE
CERTIFICATE OF CORRECTION

PATENT NO. : 4,148,906
DATED : Apr. 10, 1979
INVENTOR(S) : Platon J. Collipp

It is certified that error appears in the above-identified patent and that said Letters Patent are hereby corrected as shown below:

Col. 4, line 54, delete "5-(chlorophenyl)-" and insert in its place -- 5-(p-chlorophenyl)- --.

Signed and Sealed this

Eleventh Day of September 1979

[SEAL]

Attest:

LUTRELLE F. PARKER
*Attesting Officer*   *Acting Commissioner of Patents and Trademarks*